(12) United States Patent
Schülein et al.

(10) Patent No.: US 7,256,030 B1
(45) Date of Patent: Aug. 14, 2007

(54) FAMILY 9 ENDO-β-1,4-GLUCANASES

(75) Inventors: Martin Schülein, Copenhagen (DK); Mads Eskelund Bjørnvad, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/576,778

(22) Filed: May 23, 2000

Related U.S. Application Data

(60) Provisional application No. 60/137,295, filed on Jun. 3, 1999.

(30) Foreign Application Priority Data

May 28, 1999 (DK) ........................ 1999 00755

(51) Int. Cl.
*C12N 9/00* (2006.01)
*C12N 9/24* (2006.01)
*D06M 16/00* (2006.01)
*C07G 17/00* (2006.01)
*D21C 1/00* (2006.01)

(52) U.S. Cl. ............... 435/209; 435/183; 435/200; 435/264; 435/267; 435/274; 435/277

(58) Field of Classification Search ............... 435/183, 435/200, 209, 267, 264, 274, 277
See application file for complete search history.

(56) References Cited

FOREIGN PATENT DOCUMENTS

| | | |
|---|---|---|
| EP | 0 270 974 A2 | 6/1988 |
| EP | 0 307 564 | 3/1989 |
| EP | 0 435 876 | 6/1994 |
| GB | 368599 | 3/1932 |
| WO | WO 91/10732 | 7/1991 |
| WO | WO 91/17243 | 11/1991 |
| WO | WO 91/17244 | 11/1991 |
| WO | WO 95/24471 | 9/1995 |
| WO | WO 95/26398 | 10/1995 |

OTHER PUBLICATIONS

Gilkes et al., Microbiological Reviews, vol. 55, No. 2, pp. 303–315 (Jun. 1991).
Gilbert et al., Journal of General Microbiology, vol. 139, pp. 187–194 (1993).
Henrissat, Biochem. J., vol. 280, pp. 309–316 (1991).
Henrissat et al., Biochem. J., vol. 293, pp. 781–788 (1993).
Abstract of Dhillon et al., Biotechnol Lett 7, vol. 9, pp. 695–697 (1985).
Abstract of Jun et al., Bioscience Biotechnology and Biochemistry, vol. 61, No. 12, pp. 2004–2009 (1997).
Abstract of Sharma et al., Enzyme Microb Technol 12, vol. 2, pp. 132–137 (1990).

*Primary Examiner*—Rebecca E. Prouty
*Assistant Examiner*—Manjunath N. Rao
(74) *Attorney, Agent, or Firm*—Elias J. Lambins

(57) ABSTRACT

An enzyme exhibiting endo-β-1,4-glucanase activity which belongs to family 9 of glycosyl hydrolases is obtainable from or endogeneous to a strain belonging to the genus Bacillus such as *Bacillus licheniformis*, ATCC 14580; an isolated polynucleotide (DNA) molecule encoding an enzyme or enzyme core (the catalytically active domain of the enzyme) exhibiting endo-β-1,4-glucanase activity selected from (a) polynucleotide molecules comprising a nucleotide sequence as shown in SEQ ID NO:1 from nucleotide 76 to nucleotide 1455 or from nucleotide 76 to nucleotide 1941, (b) polynucleotide molecules that encode a polypeptide being at least 75% identical to the amino acid sequence of SEQ ID NO:2 from amino acid residue 26 to amino acid 485 or from amino acid residue 26 to amino acid residue 646, and (c) degenerate nucleotide sequences of (a) or (b), the expressed endoglucanase enzyme being useful in various industrial applications.

18 Claims, No Drawings

FAMILY 9 ENDO-β-1,4-GLUCANASES

CROSS-REFERENCE TO RELATED APPLICATIONS

This application claims priority under 35 U.S.C. 119 of Danish application no. PA 1999 00755 filed on May 28, 1999, and U.S. provisional application No. 60/137,295 filed on Jun. 3, 1999, the contents of which are fully incorporated herein by reference.

The present invention relates to an enzyme exhibiting endo-β-1,4-glucanase activity which enzyme belongs to family 9 of glycosyl hydrolases and is at least 75% homologous to a *Bacillus licheniformis* family 9 endo-β-1,4-glucanase, to an isolated polynucleotide molecule encoding such an endo-β-1,4-glucanase, and use of the enzyme in the detergent, paper and pulp, oil drilling, oil extraction, wine and juice, food ingredients, animal feed or textile industries.

BACKGROUND OF THE INVENTION

Cellulose is a polymer of glucose linked by β-1,4-glucosidic bonds. Cellulose chains form numerous intra- and intermolecular hydrogen bonds, which result in the formation of insoluble cellulose microfibrils. Microbial hydrolysis of cellulose to glucose involves the following three major classes of cellulases: (i) endoglucanases (EC 3.2.1.4) which cleave β-1,4-glucosidic links randomly throughout cellulose molecules; (ii) cellobiohydrolases (EC 3.2.1.91) which digest cellulose from the nonreducing end, releasing cellobiose; and (iii) β-glucosidases (EC 3.2.1.21) which hydrolyse cellobiose and low-molecular-mass cellodextrins to release glucose.

Cellulases are produced by many microorganisms and are often present in multiple forms. Recognition of the economic significance of the enzymatic degradation of cellulose has promoted an extensive search for microbial cellulases which can be used industrially. As a result, the enzymatic properties and the primary structures of a large number of cellulase have been investigated. On the basis of the results of a hydrophobic cluster analysis of the amino acid sequence of the catalytic domain, these cellulases have been placed into different families of glycosyl hydrolases; fungal and bacterial glycosyl hydrolases have been grouped into 35 families (Henrissat et. al. (1991), (1993)). Most cellulases consist of a cellulose-binding domain (CBD) and a catalytic domain (CAD) separated by a linker which may be rich in proline and hydroxy amino residues. Another classification of cellulases has been established on the basis of the similarity of their CBDs (Gilkes et al. (1991)) giving five families of glycosyl hydrolases (I–V).

Cellulases are synthesized by a large number of microorganisms which include fungi, actinomycetes, myxobacteria and true bacteria but also by plants. Especially endo-β-1,4-glucanases of a wide variety of specificities have been identified. Many bacterial endoglucanases have been described (Henrissat (1993); Gilbert et al.,(1993)).

An important industrial use of cellulolytic enzymes is the use for treatment of paper pulp, e.g. for improving the drainage or for deinking of recycled paper. Another important industrial use of cellulolytic enzymes is the use for treatment of cellulosic textile or fabric, e.g. as ingredients in detergent compositions or fabric softener compositions, for bio-polishing of new fabric (garment finishing), and for obtaining a "stone-washed" look of cellulose-containing fabric, especially denim, and several methods for such treatment have been suggested, e.g. in GB-A-1 368 599, Ep-A-0 307 564 and Ep-A-0 435 876, WO 91/17243, WO 91/10732, WO 91/17244, PCT/DK95/000108 and PCT/DK95/00132.

There is an ever existing need for providing novel cellulase enzymes or enzyme preparations which may be used for applications where cellulase, preferably an endo-β-1,4-glucanase, activity (EC 3.2.1.4) is desirable.

The object of the present invention is to provide novel enzymes and enzyme compositions having substantial cellulolytic activity under slightly acidic to alkaline conditions and improved performance in paper pulp processing, textile treatment, laundry processes, extraction processes or in animal feed; preferably such novel well-performing endoglucanases are producible or produced by using recombinant techniques in high yields.

SUMMARY OF THE INVENTION

The inventors have found a novel enzyme having substantial cellulolytic activity, i.e. an endo-β-1,4-glucanase (classified according to the Enzyme Nomenclature as EC 3.2.1.4), which enzyme is endogenous to *Bacillus licheniformis* and belongs to family 9 of glycosyl hydrolases, and the inventors have succeeded in cloning and expressing a DNA sequence encoding such an enzyme.

Accordingly, in its first aspect the present invention relates to an enzyme exhibiting endo-β-1,4-glucanase activity (EC 3.2.1.4) which is selected from one of (a) a polypeptide encoded by the DNA sequence of positions 76 to 1455 of SEQ ID NO:1; (b) a polypeptide produced by culturing a cell comprising the sequence of SEQ ID NO:1 under conditions wherein the DNA sequence is expressed; (c) an endo-β-1,4-glucanase enzyme having a sequence of at least 75% identity to positions 26–485 of SEQ ID NO:2 polypeptide comprising an amino acid sequence derived from the amino acid sequence of positions 26–485 of SEQ ID NO:2 when identity is determined by GAP provided in the GCG program package using a GAP creation penalty of 3.0 and GAP extension penalty of 0.1; and (d) a polypeptide encoded by the endoglucanase encoding part of the DNA sequence obtainable from the plasmid in *Escherichia coli* DSM 12805. The enzyme of the invention is identified as belonging to family 9 of glycosyl hydrolases as defined by Henrissat et al.

In its second aspect the invention relates to an isolated polynucleotide molecule, preferably a DNA molecule, encoding the catalytically active domain of an enzyme exhibiting endo-β-1,4-glucanase activity which molecule is selected from the group consisting of (a) polynucleotide molecules comprising a nucleotide sequence as shown in SEQ ID NO:1 from nucleotide 76 to nucleotide 1455, (b) species homologs of (a); (c) polynucleotide molecules that encode a polypeptide that is at least 75% identical to the amino acid sequence of SEQ ID NO:2 from amino acid residue 26 to amino acid residue 485, and (c) degenerate nucleotide sequences of (a) or (b); preferably a polynucleotide molecule capable of hybridizing to a denatured double-stranded DNA probe under medium stringency conditions, wherein the probe is selected from the group consisting of DNA probes comprising the sequence shown in positions 76–1455 of SEQ ID NO:1 and DNA probes comprising a subsequence of positions 76–1455 of SEQ ID NO:1 having a length of at least about 100 base pairs.

A plasmid pSJ1678 comprising a DNA sequence encoding the endoglucanase of the invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on May 14, 1999 under the deposition number DSM 12805.

In its third, fourth and fifth aspect the invention provides an expression vector comprising a DNA segment which is e.g. a polynucleotide molecule of the invention; a cell comprising the DNA segment or the expression vector; and a method of producing an enzyme exhibiting cellulolytic activity, which method comprises culturing the cell under conditions permitting the production of the enzyme, and recovering the enzyme from the culture.

In yet another aspect the invention provides an isolated enzyme exhibiting cellulolytic activity, characterized in (i) being free from homologous impurities and (ii) the enzyme is produced by the method described above.

Further, the present invention relates to the use of such an enzyme or the enzyme preparation of the invention for industrial applications such as for the treatment of wooden pulp or degradation of biomass.

The invention also relates to an isolated substantially pure biological culture of the *Escherichia coli* strain DSM 12805 harbouring the endoglucanase encoding DNA sequence cloned into plasmid pSJ1678 present in *Escherichia coli* DSM 12805 which is derived from a strain of the bacterial species *Bacillus licheniformis*, or any mutant of said *E.coli* strain.

The endoglucanase of the invention is advantageous in a number of industrial applicaitons by having a high specific activity on CMC (endoglucanase) and, in contrast to most other endoglucanases, the enzyme of the invention is able to degrade highly crystalline cellulose. Furthermore, this enzyme has its optimal temperature at 60° C. and is fully active between pH 5.5 and 9.5. Accordingly, the enzyme of the invention can advantageously be used for total biomass degradation, which normally would need both cellobiohydrolase(s) (which has very little activity on CMC) and endoglucanase(s).

DETAILED DESCRIPTION OF THE INVENTION

The term "glycosyl hydrolase family" as used herein has been described in Henrissat, B. "A classification of glycosyl hydrolases based of amino-acid sequence similarities." Biochem. J. 280: 309–316 (1991); Henrissat, B., Bairoch, A. "New families in the classification of glycosyl hydrolases based on amino-acid sequence similarities. Biochem. J. 293: 781–788 (1993); Henrissat, B., Bairoch, A. "Updating the sequence-based classification of glycosyl hydrolases." Biochem. J. 316: 695–696 (1996); and-Davies, G., Henrissat, B. "Structures and mechanisms of glycosyl hydrolases." Structure 3: 853–859 (1995); all of which are incorporated by reference.

The term "functional enzymatic properties" as used herein is intended to mean physical and chemical properties of a polypeptide exhibiting one or more catalytic activities. Examples of functional enzymatic properties are enzymatic activity, specific enzymatic activity, relative enzymatic activity to the maximum activity (measured as a function of either pH or temperature), stability (degradation of enzymatic activity over time), DSC melting temperature, N-terminal amino acid sequence, molecular weight (usually measured in SDS-pAGE), isoelectric point (pI).

In the present context the term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinant expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

Polynucleotides

Within preferred embodiments of the invention an isolated polynucleotide of the invention will hybridize to similar sized regions of SEQ ID NO. 1, or a sequence complementary thereto, under at least medium stringency conditions.

In particular polynucleotides of the invention will hybridize to a denatured double-stranded DNA probe comprising either the full sequence encoding for the catalytic domain of the enzyme which sequence is shown in positions 76–1455 of SEQ ID NO:1 or any probe comprising a subsequence of SEQ ID NO:1 having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×109 cpm/µg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having endoglucanase activity of the invention are then identified and isolated by, for example, hybridization or PCR.

The present invention further provides counterpart polypeptides and polynucleotides from different bacterial strains (orthologs or paralogs). Of particular interest are endoglucanase polypeptides from gram-positive alkalophilic strains, including species of Bacillus.

Species homologues of a polypeptide with endoglucanase activity of the invention can be cloned using information and compositions provided by the present invention in combination with conventional cloning techniques. For example, a DNA sequence of the present invention can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA sequence of the invention encoding an polypeptide having endoglucanase activity can then be isolated by a variety of methods, such as by probing with probes designed from the sequences disclosed in the present specification and claims or with one or more sets of degenerate probes based on the disclosed sequences. A DNA sequence of the invention can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the endoglucanase cloned from *B.licheniformis*, ATCC 14580, expressed and purified as described in Materials and Methods and Examples 1 and 3, or by an activity test relating to a polypeptide having endoglucanase activity.

The endoglucanase encoding part of the DNA sequence cloned into plasmid pSJ1678 present in *Escherichia coli* DSM 12805 and/or an analogue DNA sequence of the invention may be cloned from a strain of the bacterial species *Bacillus licheniformis*, preferably the strain ATCC 14580, producing the enzyme with endoglucanase activity, or another or related organism as described herein.

Alternatively, the analogous sequence may be constructed on the basis of the DNA sequence obtainable from the plasmid present in *Escherichia coli* DSM 12805 (which is believed to be identical to the attached SEQ ID NO:1), e.g. be a sub-sequence thereof, and/or by introduction of nucleotide substitutions which do not give rise to another amino acid sequence of the endoglucanase encoded by the DNA sequence, but which corresponds to the codon usage of the host organism intended for production of the enzyme, or by introduction of nucleotide substitutions which may give rise to a different amino acid sequence (i.e. a variant of the enzyme of the invention).

Alternatively, the DNA encoding an endoglucanase of the invention may, in accordance with well-known procedures, conveniently be cloned from a suitable source, such as any of the below mentioned organisms, by use of synthetic oligonucleotide probes prepared on the basis of the DNA sequence obtainable from the plasmid present in *Escherichia coli* DSM 12805.

How to use a sequence of the invention to get other related sequences: The disclosed sequence information herein relating to a polynucleotide sequence encoding an endo-beta-1, 4-glucanase of the invention can be used as a tool to identify other homologous endoglucanases. For instance, polymerase chain reaction (PCR) can be used to amplify sequences encoding other homologous mannanases from a variety of microbial sources, in particular of different Bacillus species.

Polypeptides

The sequence of amino acids in position 26 to about position 485 of SEQ ID NO: 2 is a mature endoglucanase sequence of the catalytic active domain. The enzyme further comprises a cellulose binding domain (CBD) which is operably linked to the catalytic active domain and which is represented by an amino acid sequence corresponding to from about position 485 to position 646 of SEQ ID NO:2. The CBD of the present endoglucanase belongs to family 3b, cf. below.

The present invention also provides endoglucanase polypeptides that are substantially homologous to the polypeptide of SEQ ID NO:2 and species homologs (paralogs or orthologs) thereof. The term "substantially homologous" is used herein to denote polypeptides having 75%, preferably at least 80%, more preferably at least 85%, and even more preferably at least 90%, sequence identity to the sequence shown in amino acids nos. 26–485 or nos. 26–646 of SEQ ID NO:2 or their orthologs or paralogs. Such polypeptides will more preferably be at least 95% identical, and most preferably 98% or more identical to the sequence shown in amino acids nos. 26–646 of SEQ ID NO:2 or its orthologs or paralogs. Percent sequence identity is determined by conventional methods, by means of computer programs known in the art such as GAP provided in the GCG program package (program Manual for the Wisconsin package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino- terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a polypeptide of the invention having endoglucanase activity.

TABLE 1

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the endoglucanase polypeptides of the present invention can be identified according to procedures known in the art, such as site-directed mutagenesis or alaninescanning mutagenesis (Cunningham and Wells, *Science* 244: 1081–1085, 1989). In the latter technique, single alanine mutations are introduced at every residue in the molecule, and the resultant mutant molecules are tested for biological activity (i.e endoglucanase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 26 to about 485 or residues 26 to 646 of SEQ ID NO: 2 and retain the endoglucanase activity of the wild-type protein.

The endoglucanase enzyme of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part the encoded enzyme as described above and in the appended SEQ ID NO:2, or a CBD from another origin may be introduced into the endoglucanase thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases (endoglucanases), xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the endoglucanase and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of a polypeptide encoded by the first or second DNA sequence of the invention.

In a preferred embodiment, the isolated polynucleotide molecule of the invention comprises a partial DNA sequence encoding a cellulose binding domain (CBD). An example of such a partial DNA sequence is the sequence corresponding to the nucleotides in positions from about 485 to 1941 of SEQ ID NO:1 or the CBD encoding part of the DNA sequence cloned into the plasmid pSJ1678 present in *Escherichia coli*, DSM 12805. The isolated polynucleotide molecule of the invention may comprise a further partial nucleotide sequence encoding a linking region, the linking region operably linking the cellulose binding domain (CBD) and the catalytically active domain (CAD) of the enzyme encoded by the nucleotide sequence comprised by the isolated polynucleotide molecule. Preferably, the linking region consists of from about 2 amino acid residues to about 120 amino acid residues, especially 10–80 amino acid residues.

Immunological Cross-reactivity

Polyclonal antibodies, especially monospecific polyclonal antibodies, to be used in determining immunological cross-reactivity may be prepared by use of a purified cellulolytic enzyme. More specifically, antiserum against the endoglucanase of the invention may be raised by immunizing rabbits (or other rodents) according to the procedure described by N. Axelsen et al. in: A Manual of Quantitative Immunoelectrophoresis, Blackwell Scientific publications, 1973, Chapter 23, or A. Johnstone and R. Thorpe, Immunochemistry in practice, Blackwell Scientific Publications, 1982 (more specifically p. 27–31). Purified immunoglobulins may be obtained from the antisera, for example by salt precipitation (($NH_4)_2$ $SO_4$), followed by dialysis and ion exchange chromatography, e.g. on DEAE-Sephadex. Immunochemical characterization of proteins may be done either by Ouchterlony double-diffusion analysis (O. Ouchterlony in: Handbook of Experimental Immunology (D.M. Weir, Ed.), Blackwell Scientific publications, 1967, pp. 655–706), by crossed immunoelectrophoresis (N. Axelsen et al., supra, Chapters 3 and 4), or by rocket immunoelectrophoresis (N. Axelsen et al., Chapter 2).

Microbial Sources

For the purpose of the present invention the term "obtained from" or "obtainable from" as used herein in connection with a specific source, means that the enzyme is produced or can be produced by the specific source, or by a cell in which a gene from the source have been inserted.

It is at present contemplated that the cellulase of the invention may be obtained from a gram-positive bacterium belonging to a strain of the genus Bacillus, in particular a strain of *Bacillus licheniformis*.

In a preferred embodiment, the cellulase of the invention is obtained from the strain Bacillus licheniformis, ATCC 14580. It is at present contemplated that a DNA sequence encoding an enzyme homologous to the enzyme of the invention may be obtained from other strains belonging to the genus Bacillus.

An isolate of a strain of *Bacillus licheniformis* from which an endo-β-1,4-glucanase of the invention can be derived is publicly available from American Type Culture Collection (ATCC) under the deposition number ATCC 14580.

Further, the plasmid pSJ1678 comprising the DNA sequence encoding the endoglucanase of the invention has been transformed into a strain of the *Escherichia coli* and deposited under the deposition number DSM 12805.

Recombinant Expression Vectors

A recombinant vector comprising a DNA construct encoding the enzyme of the invention may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome in part or in its entirety and replicated together with the. chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence, which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cells

The cloned DNA molecule introduced into the host cell may be either homologous or heterologous to the host in question. If homologous to the host cell, i.e. Produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the cloned DNA molecule or the recombinant vector of the invention is introduced may be any cell which is capable of producing the desired enzyme and includes bacteria, yeast, fungi and higher eukaryotic cells.

Examples of bacterial host cells which on cultivation are capable of producing the enzyme of the invention may be a gram-positive bacteria such as a strain of Bacillus, in particular *Bacillus alkalophilus, Bacillus amyloliquefaciens, Bacillus brevis, Bacillus lautus, Bacillus lentus, Bacillus licheniformis, Bacillus circulans, Bacillus coagulans, Bacillus megatherium, Bacillus stearothermophilus, Bacillus subtilis* and *Bacillus thuringiensis*, a strain of Lactobacillus, a strain of Streptococcus, a strain of Streptomyces, in particular *Streptomyces lividans* and *Streptomyces murinus*, or the host cell may be a gram-negative bacteria such as a strain of *Escherichia coli*.

The transformation of the bacteria may be effected by protoplast transformation, electroporation, conjugation, or by using competent cells in a manner known per se (cf. e.g. Sambrook et al., supra).

When expressing the enzyme in a bacterium such as *Escherichia coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in a gram-positive bacterium such as a strain of Bacillus or a strain of Streptomyces, the enzyme may be retained in the cytoplasm, or may be directed to the extracellular medium by a bacterial secretion sequence.

Examples of a fungal host cell which on cultivation are capable of producing the enzyme of the invention is e.g. a strain of Aspergillus or *Fusarium*, in particular *Aspergillusawamori, Aspergillus nidulans, Aspergillus niger, Aspergillus oryzae*, and *Fusarium oxysporum*, and a strain of Trichoderma, preferably *Trichoderma harzianum, Trichoderma reesei* and *Trichoderma viride*.

Fungal cells may be transformed by a process involving protoplast formation and transformation of the protoplasts followed by regeneration of the cell wall in a manner known per se. The use of a strain of Aspergillus as a host cell is described in Ep 238 023 (Novo Nordisk A/S), the contents of which are hereby incorporated by reference.

Examples of a host cell of yeast origin which on cultivation are capable of producing the enzyme of the invention is e.g. a strain of Hansenula sp., a strain Of Kluyveromyces sp., in particular *Kluyveromyces lactis* and *Kluyveromyces marcianus*, a strain of pichia sp., a strain of Saccharomyces, in particular *Saccharomyces carlsbergensis, Saccharomyces cerevisae, Saccharomyces kluyveri* and *Saccharomyces uvarum*, a strain of Schizosaccharomyces sp., in particular *Schizosaccharomyces pombe*, and a strain of Yarrowia sp., in particular *Yarrowia lipolytica*.

Examples of a host cell of plant origin which on cultivation are capable of producing the enzyme of the invention is e.g. a plant cell of *Solanum tuberosum* or *Nicotiana tabacuin*.

Method of Producing a Cellulolytic Enzyme

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

As defined herein, an isolated polypeptide (e.g. an enzyme) is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The term "isolated polypeptidel" may alternatively be termed "purified polypeptide".

When an expression vector comprising a DNA sequence encoding the enzyme is transformed into a heterologous host cell it is possible to enable heterologous recombinant production of the enzyme of the invention.

Thereby it is possible to make a highly purified or monocomponent cellulolytic composition, characterized in being free from homologous impurities.

In this context, homologous impurities mean any impurities (e.g. other polypeptides than the enzyme of the invention) which originate from the homologous cell where the enzyme of the invention is originally obtained from.

In the present invention the homologous host cell may be a strain of Bacillus licheniformis.

The medium used to culture the transformed host cells may be any conventional medium suitable for growing the host cells in question. The expressed cellulolytic enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme Compositions

In a still further aspect, the present invention relates to an enzyme composition comprising an enzyme exhibiting endoglucanase activity as described above.

The enzyme composition of the invention may, in addition to the endoglucanase of the invention, comprise one or more other enzyme types, for instance hemicellulase such as xylanase and mannanase, other cellulase or endo-β-1,4-glucanase components, chitinase, lipase, esterase, pectinase, cutinase, phytase, oxidoreductase (peroxidase, haloperoxidase, oxidase, laccase), protease, amylase, reductase, phenoloxidase, ligninase, pullulanase, pectate lyase, xyloglucanase, pectin acetyl esterase, polygalacturonase, rhamnogalacturonase, pectin lyase, pectin methylesterase, cellobiohydrolase, transglutaminase; or mixtures thereof.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Endoglucanases have potential uses in a lot of different industries and applications. Examples are given below of preferred uses of the enzyme composition of the invention. The dosage of the enzyme composition of the invention and other conditions under which the composition is used may be determined on the basis of methods known in the art.

The enzyme composition according to the invention may be useful for at least one of the following purposes.

The Enzyme

In a preferred embodiment of the present invention, the endoglucanase exhibits activity at a pH in the range of 4–11, preferably 5.5–10.5.

Uses

Biomass Degradation

The enzyme or the enzyme composition according to the invention may be applied advantageously e.g. as follows:

For debarking, i.e. pretreatment with hydrolytic enzymes which may partly degrade the pectin-rich cambium layer prior to debarking in mechanical drums resulting in advantageous energy savings.

For defibration (refining or beating), i.e. treatment of material containing cellulosic fibers with hydrolytic enzymes prior to the refining or beating which results in reduction of the energy consumption due to the hydrolysing effect of the enzymes on the surfaces of the fibers.

For fibre modification, i.e. improvement of fibre properties where partial hydrolysis across the fibre wall is needed which requires deeper penetrating enzymes (e.g. in order to make coarse fibers more flexible).

For drainage: The drainability of papermaking pulps may be improved by treatment of the pulp with hydrolysing enzymes. Use of the enzyme or enzyme composition of to the invention may be more effective, e.g. result in a higher degree of loosening bundles of strongly hydrated micro-fibrils in the fines fraction that limits the rate of drainage by blocking hollow spaces between the fibers and in the wire mesh of the paper machine.

The treatment of lignocellulosic pulp may, e.g., be performed as described in WO 93/08275, WO 91/02839 and WO 92/03608.

Use in the Detergent Industry

The enzyme or enzyme composition of the invention may be useful in a detergent composition for house-hold or industrial laundering of textiles and garment, and to a process for machine treatment of fabrics comprising treating fabric during a washing cycle of a machine washing process with a washing solution containing the enzyme or enzyme preparation of the invention.

Typically, the detergent composition of the invention comprises conventional ingredients such as surfactants (anionic, nonionic, zwitterionic, amphoteric), builders, and other ingredients, e.g. as described in WO 97/01629 which is hereby incorporated by reference.

Textile Applications

In another embodiment, the present invention relates to use of the endoglucanase of the invention in the biopolishing process. Bio-polishing is a specific treatment of the yarn surface which improves fabric quality with respect to handle and appearance without loss of fabric wettability. The most important effects of Bio-Polishing can be characterized by less fuzz and pilling, increased gloss/luster, improved fabric handle, increased durable softness and altered water absorbency. Bio-Polishing usually takes place in the wet processing of the manufacture of knitted and woven fabrics. Wet processing comprises such steps as e.g. desizing, scouring, bleaching, washing, dying/printing and finishing. During each of these steps, the fabric is more or less subjected to mechanical action. In general, after the textiles have been knitted or woven, the fabric proceeds to a desizing stage, followed by a scouring stage, etc. Desizing is the act of removing size from textiles. Prior to weaving on mechanical looms, warp yarns are often coated with size starch or starch derivatives in order to increase their tensile strength. After weaving, the size coating must be removed before further processing the fabric in order to ensure a homogeneous and wash-proof result. It is known that in order to achieve the effects of Bio-Polishing, a combination of cellulytic and mechanical action is required. It is also known that "super-softness" is achievable when the treatment with a cellulase is combined with a conventional treatment with softening agents. It is contemplated that use of the endoglucanase of the invention for bio-polishing of cellulosic fabrics is advantageous, e.g. a more thorough polishing can be achieved. Bio-polishing may be obtained by applying the method described e.g. in WO 93/20278.

Stone-washing

It is known to provide a "stone-washed" look (localized abrasion of the colour) in dyed fabric, especially in denim fabric or jeans, either by washing the denim or jeans made from such fabric in the presence of pumice stones to provide the desired localized lightening of the colour of the fabric or by treating the fabric enzymatically, in particular with cellulytic enzymes. The treatment with an endoglucanase of the present invention may be carried out either alone such as disclosed in U.S. Pat. No. 4,832,864, together with a smaller amount of pumice than required in the traditional process, or together with perlite such as disclosed in WO 95/09225.

Determination of CMC Units

CMC units is determined using 0.1 M Mops buffer pH.7.5 at 60° C. 20 min incubation and determination of the formation of reducing sugars using PHAB. One CMC unit corresponds to the formation of 1 micromole glucose equivalent per min. The CMC (Carboxy Methyl Cellulose 7L from Hercules) final concentration is 0.75%, DS 0.7.

Materials and Methods

Strains

*Bacillus licheniformis* ATCC 14580.

*B.subtilis* PL2306. This strain is the *B.subtilis* DN1885 with disrupted apr and npr genes (Diderichsen et al. (1990)) disrupted in the transcriptional unit of the known *Bacillus subtilis* cellulase gene, resulting in cellulase negative cells. The disruption was performed essentially as described in A.L. Sonenshein et al. (1993).

Competent cells were prepared and transformed as described by Yasbin et al. (1975).

Plasmids pSJ1678 disclosed in International Patent Publication WO 94/19454.

pMOL944

This plasmid is a pUB110 derivative essentially containing elements making the plasmid propagatable in *Bacillus subtilis*, kanamycin resistance gene and having a strong promoter and signal peptide cloned from the amyL gene of *B.licheniformis* ATCC14580. The signal peptide contains a SacII site making it convenient to clone the DNA encoding the mature part of a protein in-fusion with the signal peptide. This results in the expression of a pre-protein, which is directed towards the exterior of the cell.

The plasmid was constructed by means of conventional genetic engineering techniques, which are briefly described in the following.

Construction of pMOL944

The pUB110 plasmid (McKenzie, T. et al., 1986) was digested with the unique restriction enzyme NciI. A PCR fragment amplified from the amyL promoter encoded on the plasmid pDN1981 (Jørgensen P.L. et al. (1990)) was digested with NciI and inserted in the NciI digested pUB110 to give the plasmid pSJ2624. The two PCR primers used have the following sequences:

LWN5494 5'-GTCGCCGGGGCGGCCGCTATCAATT GGTAACTGTATCTCAGC-3'(SEQ ID NO:1)

LWN5495 5'-GTCGCCCGGGAGCTCTGATCAGGTA CCAAGCTTGTCGACCTGCAGAATGAGGCAGCAA GAAGAT-3'(SEQ ID NO:2)

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

LWN5938 5'-GTCGGCGGCCGCTGATCACGTACC AAGCTTGTCGACCTGCAGAATGAGGCAGCAAG AAGAT-3'(SEQ ID NO:3)

LWN5939 5'-GTCGGAGCTCTATCAATTGGTAACTGT ATCTCAGC-3'(SEQ ID NO:4)

The plasmid pSJ2670 was digested with the restriction enzymes pstI and BclI and a PCR fragment amplified from a cloned DNA sequence encoding the alkaline amylase SP722 (disclosed in the International Patent Application published as WO95/26397 which is hereby incorporated by reference in its entirety) was digested with pstI and BclI and inserted to give the plasmid pMOL944. The two primers used for PCR amplification have the following sequence:

LWN7864 5'-AACAGCTGATCACGACTGATCTTTT AGCTTGGCAC-3'(SEQ ID NO:5)

LWN7901 5'-AACTGCAGCCGCGGCACATCATAAT GGGACAAATGGG-3'(SEQ ID NO:6)

The primer #LWN7901 inserts a SacII site in the plasmid.

General Molecular Biology Methods

Unless otherwise mentioned the DNA manipulations and transformations were performed using standard methods of molecular biology (Sambrook et al. (1989); Ausubel, F. M. et al. (eds) (1995); Harwood, C. R., and Cutting, S. M. (eds.) (1990)).

Enzymes for DNA manipulations were used according to the specifications of the suppliers (e.g. restriction endonucleases, ligases etc. are obtainable from New England Biolabs, Inc.).

Media

TY (as described in Ausubel et al. (1995)).

LB agar (as described in Ausubel et al. (1995)).

LBPG is LB agar supplemented with 0.5% glucose and 0.05 M potassium phosphate, pH 7.0

BPX media is described in Ep 0 506 780 (WO 91/09129).

The following examples illustrate the invention.

EXAMPLE 1

Cloning and Expression of Endo-beta-1,4-glucanase from *Bacillus Licheniformis*

Genomic DNA Preparation

Strain *Bacillus licheniformis* ATCC 14580 was propagated in liquid medium 3 as specified by ATCC (American Type Culture Collection, USA). After 18 hours incubation at 37°C. and 300 rpm, the cells were harvested, and genomic DNA isolated by the method described by pitcher et al. (1989).

Genomic Library Construction

Genomic DNA of *Bacillus licheniformis* ATCC 14580 was partially digested with restriction enzyme Sau3A and size-fractionated by electrophoresis on a 0.7% agarose gel. Fragments of between 2 and 7 kb in size were isolated by electrophoresis onto DEAE-cellulose paper (Dretzen et al. (1981)). Isolated DNA fragments were ligated to BamHI digested pSJ1678 plasmid DNA.

Ligated DNA was used in electroporation of *E.coli* SJ2, the transformed cells were plated on LB-agar plates containing 10 mg/ml Chloramphenicol and 0.1% CMC (Sodium-Carboxy-Methyl-Cellulose, Aqualon, France), the plates were incubated 18 hours at 37° C.

Identification of Positive Clones by Colony Hybridization

A DNA library in *E. coli* constructed as described above, was screened on LB agar plates containing 0.1% CMC (Sodium-Carboxy-Methyl-Cellulose, Aqualon, France) and 10 µg/ml Chloramphenicol and incubated overnight at 37° C. The transformants were subsequently replica plated onto the same type of plates, and these new plates were incubated 8 hours or overnight at 37° C.

The original plates were coloured using 25 ml of a aqueous solution containing 1 mg/ml of Congo Red (SIGMA, USA). The colouring was continued for half an hour with moderate orbital shaking, after which the plates were washed two times 15 minutes using 1 M NaCl.

Yellowish halos appeared at positions where cellulase positive clones were present, from the replica plates these cellulase positive clones were rescued and re-streaked onto LB agar plates containing 0.1% CMC and 9 µg/ml Chloramphenicol and incubated overnight at 37° C.

Characterization of Positive Clones

From the re-streaking plates the endoglucanase positive clones were obtained as single colonies, and plasmids were extracted. Phenotypes were confirmed by retransformation of *E.coli* SJ2, and plasmids characterized by restriction digests. One positive clone was termed MB629-3.

The endoglucanase gene was characterized by DNA sequencing using the Taq deoxy-terminal cycle sequencing kit (Perkin-Elmer, USA) and performing primer walking, starting with primers unique to the pSJ1678 plasmid and on each side of the cloned endoglucanase encoding DNA fragment.

Analysis of the sequence data was performed according to Devereux et al. (1984). The sequence corresponds to the DNA sequence shown in SEQ ID NO: 1.

The DNA sequence of the invention coding for the family 9 endo-beta-1,4-glucanase represented by amino acid sequence SEQ ID NO:2 (also denoted Cel9) was PCR amplified using the PCR primer set consisting of these two oligo nucleotides:

Cel9.B.lich.upper.PstI
5'-CAT CAT TCT GCA GCC GCG GCA GCT TCT GCT GAA GAA TAT CCT C-3'(SEQ ID NO:7)
Cel9.B.lich.lower.NotI
5'-GCG AGA ATA GCG GCC GCT AGT AAC CGG GCT CAT GTC CG-3'(SEQ ID NO:8)

Restriction Sites PstI and NotI are Underlined

Chromosomal DNA isolated from *B. licheniformis* ATCC 14580 as described above was used as template in a PCR reaction using Amplitaq DNA polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 µM of each dNTP, 2.5 units of AmpliTaq polymerase (Perkin-Elmer, Cetus, USA) and 100 pmol of each primer.

The PCR reactions were performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analyzed by electrophoresis in 0.7% agarose gels (NuSieve, FMC). The appearance of a DNA fragment size 2.0 kb indicated proper amplification of the gene segment.

Subcloning of PCR Fragment

Fortyfive-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. 5 µg of pMOL944 and twentyfive-µl of the purified PCR fragment was digested with PstI and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the PstI-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B.subtilis* PL2306. The transformed cells were plated onto LBPG-10 µg/ml of Kanamycin plates. After 18 hours incubation at 37° C. several clones were re-streaked on fresh agar plates and also grown in liquid TY cultures with 10 µg/ml kanamycin and incubated overnight at 37° C. Next day 1 ml of cells were used to isolate plasmid from the cells using the Qiaprep Spin Plasmid Miniprep Kit #27106 according to the manufacturers recommendations for *B.subtilis* plasmid preparations. This plasmid DNA was used as template for DNA sequencing.

One clone containing the endo-beta-1,4-glucanase gene of the invention was kept, this clone was denoted MB905.

The plasmid from MB905 was introduced to a derivative of *B.licheniformis* ATCC 14580, for expression trials. This strain was termed MB924. The cloned DNA sequence was expressed in *B.licheniformis* by fermenting the cells in BP-X media at 37° C. for 5 days at 300 rpm. The endoglucanase protein that appeared in the supernatant corresponded to the mature protein of SEQ ID NO:2, ie comprised the protein sequence corresponding to the amino acids at position 26–646 of SEQ ID NO:2.

EXAMPLE 2

Purification and Characterization of Endo-beta-1,4-glucanase from *Bacillus Licheniformis*

Purification

MB924 obtained as described in example 1 was grown in 15×200 ml BPX media with 10 µg/ml of Kanamycin in 500 ml two baffled shake flasks for 5 days at 37° C. at 300 rpm, whereby 2500 ml of culture broth was obtained. The culture fluid was diluted with one volume of ionized water and pH adjusted to 7.5, using acetic acid. Then 112.5 ml of cationic agent (C521 10%) and 225 ml of anionic agent (A130 0.1%) was added during agitation for flocculation. The flocculated material was separated by centrifugation using a Sorval RC 3B centrifuge at 10000 rpm for 30 min at 6° C. The resulting supernatant contained 120 CMCunits per ml in a total volume of 5000 ml.

The supernatant was clarified using Whatman glass filters GF/D and C and finally concentrated on a filtron UF membrane with a cut off of 10 kDa. The total volume of 1750 ml was adjusted to pH 8.0.

For obtaining a highly purified endoglucanase a final step sing Q-sepharose anion-exchange chromatography was carried out. 1750 ml of the solution was applied to a 800 ml column containing Q-Sepharose (Pharmacia) equilibrated with a buffer of 50 mol Tris pH 8.0. The endoglucanase bound and was eluted using a 5 M NaCl gradient. The more than 95% of the endoglucanase was concentrated.

Characterisation

The pure enzyme gave a single band in SDS-PAGE of 67 kDa and an isoelectric point of around 5.6.

The protein concentration was determined using a molar extinction coefficient of 171640 (based on the amino acid composition deducted from the sequence). The pH activity profiles showed more than 50% relative activity between pH 6.0 and 9.2. at 60°. The temperature optimum was 65° at pH 7.5. DSC showed melting at 77° C. at pH 6.2.

N-terminal determination of the pure endoglucanase: EYPHNYAELLQK(amino acids 30–44 of SEQ ID NO:10)

The pure endoglucanase comprises a catalytic domain belonging to family 9 of glycosyl hydrolases, which domain corresponds to the amino acid sequence from about position 26 to about position 485 of SEQ ID NO:2, and a cellulase binding domain (CBD) which is linked to the catalytic domain and is represented by the the amino acid sequence from about position 486 to position 644 of SEQ ID NO:2. The CBD belongs to family 3b.

Immunological properties: At the Danish company DAKO, rabbit polyclonal monospecific serum was raised against the highly purified endo-beta-1,4-glucanase using conventional techniques. The serum formed a nice single precipitate in agarose gels with the endoglucanase of the invention.

LITERATURE

Ausubel, F. M. et al. (eds.) "Current protocols in Molecular Biology". John Wiley and Sons, 1995.

Axelsen, N., et al. in: A Manual of Quantitative Immunoelectrophoresis, Blackwell Scientific Publications, 1973, Chapter 23.

Denman, S. et al.: Characterization of a Neocallumastix patriarum cellulase cDNA (celA) homologous to *Trichoderma reesei* cellobiohydrolase II, Appl. Environ. Microbiol. (1996), 62(6), 1889-1896.

Damude, H. G. et al.: Substrate specificity of endoglucanase A from Cellulomonas fimi: fundamental differences between endoglucanases and exoglucanases from family 6, Biochem.J. (1996), 315(2), 467–72.

Devereux et al. (1984) Nucleic Acids Res. 12, 387–395.

Diderichsen, B., Wedsted, U., Hedegaard, L., Jensen, B. R., Sjøholm, C. (1990) Cloning of aldb, which encodes alpha-acetolactate decarboxylase, an exoenzyme from *Bacillus brevis*. J. Bacteriol., 172, 4315–4321.

Dretzen, G., Bellard, M., Sassone-Corsi, P., Chambon, P. (1981) A reliable method for the recovery of DNA fragments from agarose and acrylamide gels. Anal. Biochem., 112, 295–298.

Feinberg, A. P. and Vogelstein, B. (1983) *Anal. Biochem.* 132:6–13.

Gilbert, H. J. and Hazlewood, G. P. (1993) J. Gen. Microbiol. 139:187–194.

Gilkes, N. R., Henrissat, B., Kilburn, D. G., Miller Jr., R. C. and Warren, R. A. J.: Domains in microbial β-1,4-glycanases; sequence conservation, function, and enzyme families. Microbiol. Rev. 55 (1991), 305–315.

Harwood, C. R., and Cutting, S. M. (eds.) "Molecular Biological Methods for Bacillus". John Wiley and Sons, 1990.

Henrissat, B.: A classification of glycosyl hydrolases based on amino acid sequence similarities. Biochem. J. 280 (1991), 309–316.

Henrissat, B., and Bairoch, A.: New families in the classification of glycosyl hydrolases based on amino acid sequence similarities. Biochem. J. 293 (1993), 781–788.

Johnstone, A. and R. Thorpe, Immunochemistry in Practice, Blackwell Scientific Publications, 1982 (pp. 27–31).

Jørgensen P. L. et al. (1990) Gene, 96, p.37–41.

Leatherbarrow, R. J. (1992) Grafit version 3.0 Erithacus Software Ltd. Staines, U.K.

Lever, M. (1972) A new reaction for colormetric determination of carbohydrates. *Anal. Biochem.* 47, 273–279.

McKenzie, T. et al., 1986, plasmid 15:93–103.

O. Ouchterlony in: Handbook of Experimental Immunology (D. M. Weir, Ed.), Blackwell Scientific Publications, 1967, pp. 655–706.

Pitcher, D. G., Saunders, N. A., Owen, R. J. (1989): Rapid extraction of bacterial genomic DNA with guanidium thiocyanate. Lett. Appl. Microbiol., 8, 151–156.

Quillet, L. et al.: The gene encoding the beta-1,4-endoglucanase (Cel) from *Myxococcus xanthus*: evidence for independent acquisition by horizontal transfer of binding and catalytic domains from actinomycetes, Gene (1995), 158(1), 23–9.

Sambrook et al. (1989) Molecular cloning: A laboratory manual, Cold Spring Harbor lab., Cold Spring Harbor, N.Y.

Eds. A. L. Sonenshein, J. A. Hoch and Richard Losick (1993) *Bacillus subtilis* and other Gram-positive Bacteria, American Society for microbiology, p.618.

Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296–304.

What is claimed is:

1. An isolated enzyme exhibiting beta-1,4-endoglucanase activity (EC 3.2.1.4) which (a) has a temperature optimum of 65° C. measured at a pH of 7.5 and (b)(i) has an amino acid sequence that is at least 95% identical to amino acids 1–456 or 1–617 of SEQ ID NO: 2 wherein identity is determined by GAP provided in the GCG program package using a GAP creation penalty of 3.0 and GAP extension penalty of 0.1or (ii) is encoded by a DNA sequence that hybridizes to nucleotides 76–1455 of SEQ ID NO: 1 under high stringency conditions, wherein the high stringency conditions are defined as hybridization in 5xSSC at 45° C. and washing in 2xSSC at 70° C.

2. The enzyme of claim 1, which belongs to family 9 of glycosyl hydrolases.

3. The enzyme of claim 1, which has an amino acid sequence that is at least 95% identical to amino acids 1–456 or 1–617 SEQ ID NO: 2.

4. The enzyme of claim 3, which has as amino acid sequence that is at least 98% identical to amino acids 1–456 or 1–617 of SEQ ID NO: 2.

5. The enzyme of claim 1, which comprises the amino acid sequence of amino acids 1–456 of SEQ ID NO: 2.

6. The enzyme of claim 1, which comprises the amino acid sequence of amino acids 1–617 SEQ ID NO: 2.

7. The enzyme of claim 1, which consists of the amino acid sequence of amino acids 1–456 of SEQ ID NO: 2.

8. The enzyme of claim 1, which consists of the amino acid sequence of amino acids 1–617 of SEQ ID NO: 2.

9. The enzyme of claim 1, which is encoded by a DNA sequence that hybridizes to nucleotides 76–1455 of SEQ ID NO: 1; under high stringency conditions, wherein the high stringency conditions are defined as hybridization in 5xSSC at 45 ° C. and washing in 2xSSC at 70° C.

10. The enzyme of claim 9, which is encoded by a DNA sequence that hybridizes to nucleotides 76-1455 of SEQ ID NO: 1 under high stringency conditions, wherein the high stringency conditions are defined as hybridization in 5xSSC at 45° C. and washing in 2xSSC at 75° C.

11. The enzyme of claim 1, which is a *Bacillus licheniformis*, ATCC 14580 enzyme.

12. The enzyme of claim 11, which is a *Bacillus licheniformis*, ATCC 14580 enzyme.

13. The enzyme of claim 1, which is active at a pH in the range of 4–11.

14. The enzyme of claim 13, which is active at a pH in the range of 5.5–10.5.

15. An enzyme composition comprising the enzyme of claim 1.

16. The composition of claim 15, which further comprises one or more enzymes selected from the group consisting of alpha-arnylases, cellobiohydrolases, cellulases (endoglucanases), cutinases, beta-glucanases, glucoamylases, hemicellulases, laccases, ligninases, lipases, oxidases, pectate lyases, pectin acetyl esterases, pectinases, pectin lyases, pectin methylesteases, peroxidases, phenoloxidases, polygalacturonases, proteases, pullulanases, reductases, rhamnogalacturonases, xylanases, xyloglucanases, other mannanases, transglutaminases, and mixtures thereof.

17. A method for degradation of cellulose-containing biomass, comprising treating the biomass with an effective amount of the enzyme of claim 1.

18. An isolated enzyme exhibiting beta-1,4-endoglucanase activity (EC 3.2.1.4) which has an amino acid sequence comprising amino acids 1–456 or 1–617 of SEQ ID NO: 2.

* * * * *

SEQUENCE LISTING

<160> NUMBER OF SEQ ID NOS: 10

<210> SEQ ID NO 1
<211> LENGTH: 42
<212> TYPE: DNA
<213> ORGANISM: Bacillus Licheniformis

<400> SEQUENCE: 1
gtcgccgggg cggccgctat caattggtaa ctgtatctca gc      42

<210> SEQ ID NO 2
<211> LENGTH: 64
<212> TYPE: DNA
<213> ORGANISM: Bacillus Licheniformis

```
<400> SEQUENCE: 2
gtcgcccggg agctctgatc aggtaccaag cttgtcgacc tgcagaatga ggcagcaaga    60
agat                                                                 64

<210> SEQ ID NO 3
<211> LENGTH: 61
<212> TYPE: DNA
<213> ORGANISM: Bacillus Licheniformis

<400> SEQUENCE: 3
gtcggcggcc gctgatcacg taccaagctt gtcgacctgc agaatgaggc agcaagaaga    60
t                                                                    61

<210> SEQ ID NO 4
<211> LENGTH: 35
<212> TYPE: DNA
<213> ORGANISM: Bacillus Licheniformis

<400> SEQUENCE: 4
gtcggagctc tatcaattgg taactgtatc tcagc                               35

<210> SEQ ID NO 5
<211> LENGTH: 35
<212> TYPE: DNA
<213> ORGANISM: Bacillus Licheniformis

<400> SEQUENCE: 5
aacagctgat cacgactgat cttttagctt ggcac                               35

<210> SEQ ID NO 6
<211> LENGTH: 37
<212> TYPE: DNA
<213> ORGANISM: Bacillus Licheniformis

<400> SEQUENCE: 6
aactgcagcc gcggcacatc ataatgggac aaatggg                             37

<210> SEQ ID NO 7
<211> LENGTH: 43
<212> TYPE: DNA
<213> ORGANISM: Bacillus Licheniformis

<400> SEQUENCE: 7
catcattctg cagccgcggc agcttctgct gaagaatatc ctc                      43

<210> SEQ ID NO 8
<211> LENGTH: 38
<212> TYPE: DNA
<213> ORGANISM: Bacillus Licheniformis

<400> SEQUENCE: 8
gcgagaatag cggccgctag taaccgggct catgtccg                            38

<210> SEQ ID NO 9
<211> LENGTH: 1941
<212> TYPE: DNA
<213> ORGANISM: Bacillus licheniformis

<400> SEQUENCE: 9
atgaaagcgc tttgtttggc wcttttagtg atcttctcta tgagcatagc gtcgttttca    60
```

| | |
|---|---|
| gaaaagaccc gtgcagcttc tgctgaagaa tatcctcata attatgctga actgctgcaa | 120 |
| aagtctttgt tattttatga agcacagcgc tcgggaagac ttccggaaaa cagccggctg | 180 |
| aattggagag gagactccgg gcttgaggac ggaaaagacg ttggcctcga tttaacggga | 240 |
| gggtggtatg atgccggcga ccacgtgaag ttcggtctgc cgatggctta ttctgccgca | 300 |
| atcctgtcat ggtcggtcta tgagtaccga gatgcctaca aagaatcggg tcagcttgat | 360 |
| gcggcgctgg acaatattaa atgggcgaca gactactttc ttaaagccca tacggctcct | 420 |
| tatgaattgt ggggccaagt cggaaatggc gctctagacc acgcatggtg ggggccggcc | 480 |
| gaagtaatgc cgatgaagcg ccctgcctat aagatcgatg ccggctgtcc ggggtcagac | 540 |
| cttgctggtg gtacagccgc agcgctagca tcagcatcaa ttattttcaa gccgacagat | 600 |
| tcttcttact ctgaaaaatt actggctcat gccaagcaat gtatgatttt gccgaccgc | 660 |
| taccgcggca atattcaga ctgcattaca gacgcacagc aatattataa ttcgtggagc | 720 |
| gggtataaag atgaactgac atggggagct gtctggctct acttggcaac agaagaacaa | 780 |
| caatatttgg ataaagccct tgcttcggtc tcagattggg gcgatcccgc aaactggcct | 840 |
| taccgctgga cgcttttcctg ggatgacgtc acttacggag cacagctgct gctcgctcgt | 900 |
| ctgacaaacg attccgtttt tgtcaaatct gtcgaacgca atcttgatta ttggtcgaca | 960 |
| ggctacagtc ataatggaag catagaacgg atcacgtata cgccgggcgg tttggcctgg | 1020 |
| cttgagcagt ggggatcatt gcgatacgct tcgaatgccg ctttttctcgc tttcgtttat | 1080 |
| tccgattggg tggatacaga aaaagcgaaa agatatcggg attttgctgt tcggcaaacg | 1140 |
| gagtatatgc taggagataa tccgcagcag cgaagctttg tcgttggata cggtaaaaat | 1200 |
| ccgccgaaac atccgcatca ccgtacagca cacggttcat gggccaatca gatgaatgtg | 1260 |
| cctgaaaacc atcgccatac cctatacggc gcattagtcg gcggtccggg aagggacgat | 1320 |
| tcgtaccgag atgacataac agattatgcg tcaaacgaag ttgcgatcga ttataatgcc | 1380 |
| gcttttaccg gcaacgtagc gaaaatgttt cagctgttcg ggaaaggcca tgttccgctg | 1440 |
| cctgattttc cggagaagga aacacctgag gacgaatatt ttgcagaggc atcaatcaac | 1500 |
| agctccggaa acagctatac tgaaatccgg gcgcagctca taaccgttc gggatggccg | 1560 |
| gcaaagaaaa ccgatcaatt gtcttttccgc tactacgttg acttgacgga agctgtagaa | 1620 |
| gcgggatatt ccgccgaaga tataaaagtc acagccggct ataacgaagg ggcctcggta | 1680 |
| tcagagctga agccgcatga cgcttcaaag cacatttact atacagaagt cagcttcagc | 1740 |
| ggggttttga tttatccagg cggtcaatcc gcccataaaa aagaagtgca gttccgcctt | 1800 |
| tcggcaccag acggaacgtc ttttttggaac ccggaaaatg accactctta tcagggtctg | 1860 |
| tcacatgcgc ttctgaagac gcggtatatt cctgtttatg atgatggacg gctcgttttc | 1920 |
| ggacatgagc ccggttacta g | 1941 |

<210> SEQ ID NO 10
<211> LENGTH: 646
<212> TYPE: PRT
<213> ORGANISM: Bacillus

<400> SEQUENCE: 10

Met Lys Ala Leu Cys Leu Ala Leu Leu Val Ile Phe Ser Met Ser Ile
1               5                   10                  15

Ala Ser Phe Ser Glu Lys Thr Arg Ala Ala Ser Ala Glu Glu Tyr Pro
            20                  25                  30

His Asn Tyr Ala Glu Leu Leu Gln Lys Ser Leu Leu Phe Tyr Glu Ala

```
                 35                  40                  45
Gln Arg Ser Gly Arg Leu Pro Glu Asn Ser Arg Leu Asn Trp Arg Gly
             50                  55                  60

Asp Ser Gly Leu Glu Asp Gly Lys Asp Val Gly Leu Asp Leu Thr Gly
 65                  70                  75                  80

Gly Trp Tyr Asp Ala Gly Asp His Val Lys Phe Gly Leu Pro Met Ala
                 85                  90                  95

Tyr Ser Ala Ala Ile Leu Ser Trp Ser Val Tyr Glu Tyr Arg Asp Ala
                100                 105                 110

Tyr Lys Glu Ser Gly Gln Leu Asp Ala Ala Leu Asp Asn Ile Lys Trp
            115                 120                 125

Ala Thr Asp Tyr Phe Leu Lys Ala His Thr Ala Pro Tyr Glu Leu Trp
        130                 135                 140

Gly Gln Val Gly Asn Gly Ala Leu Asp His Ala Trp Trp Gly Pro Ala
145                 150                 155                 160

Glu Val Met Pro Met Lys Arg Pro Ala Tyr Lys Ile Asp Ala Gly Cys
                165                 170                 175

Pro Gly Ser Asp Leu Ala Gly Gly Thr Ala Ala Leu Ala Ser Ala
                180                 185                 190

Ser Ile Ile Phe Lys Pro Thr Asp Ser Ser Tyr Ser Glu Lys Leu Leu
            195                 200                 205

Ala His Ala Lys Gln Leu Tyr Asp Phe Ala Asp Arg Tyr Arg Gly Lys
        210                 215                 220

Tyr Ser Asp Cys Ile Thr Asp Ala Gln Gln Tyr Tyr Asn Ser Trp Ser
225                 230                 235                 240

Gly Tyr Lys Asp Glu Leu Thr Trp Gly Ala Val Trp Leu Tyr Leu Ala
                245                 250                 255

Thr Glu Glu Gln Gln Tyr Leu Asp Lys Ala Leu Ala Ser Val Ser Asp
                260                 265                 270

Trp Gly Asp Pro Ala Asn Trp Pro Tyr Arg Trp Thr Leu Ser Trp Asp
            275                 280                 285

Asp Val Thr Tyr Gly Ala Gln Leu Leu Leu Ala Arg Leu Thr Asn Asp
        290                 295                 300

Ser Arg Phe Val Lys Ser Val Glu Arg Asn Leu Asp Tyr Trp Ser Thr
305                 310                 315                 320

Gly Tyr Ser His Asn Gly Ser Ile Glu Arg Ile Thr Tyr Thr Pro Gly
                325                 330                 335

Gly Leu Ala Trp Leu Glu Gln Trp Gly Ser Leu Arg Tyr Ala Ser Asn
            340                 345                 350

Ala Ala Phe Leu Ala Phe Val Tyr Ser Asp Trp Val Asp Thr Glu Lys
        355                 360                 365

Ala Lys Arg Tyr Arg Asp Phe Ala Val Arg Gln Thr Glu Tyr Met Leu
    370                 375                 380

Gly Asp Asn Pro Gln Gln Arg Ser Phe Val Val Gly Tyr Gly Lys Asn
385                 390                 395                 400

Pro Pro Lys His Pro His His Arg Thr Ala His Gly Ser Trp Ala Asn
                405                 410                 415

Gln Met Asn Val Pro Glu Asn His Arg His Thr Leu Tyr Gly Ala Leu
            420                 425                 430

Val Gly Gly Pro Gly Arg Asp Asp Ser Tyr Arg Asp Asp Ile Thr Asp
        435                 440                 445

Tyr Ala Ser Asn Glu Val Ala Ile Asp Tyr Asn Ala Ala Phe Thr Gly
450                 455                 460
```

```
Asn Val Ala Lys Met Phe Gln Leu Phe Gly Lys Gly His Val Pro Leu
465             470                 475                 480

Pro Asp Phe Pro Glu Lys Glu Thr Pro Glu Asp Glu Tyr Phe Ala Glu
                485                 490                 495

Ala Ser Ile Asn Ser Ser Gly Asn Ser Tyr Thr Glu Ile Arg Ala Gln
            500                 505                 510

Leu Asn Asn Arg Ser Gly Trp Pro Ala Lys Lys Thr Asp Gln Leu Ser
        515                 520                 525

Phe Arg Tyr Tyr Val Asp Leu Thr Glu Ala Val Glu Ala Gly Tyr Ser
    530                 535                 540

Ala Glu Asp Ile Lys Val Thr Ala Gly Tyr Asn Glu Gly Ala Ser Val
545             550                 555                 560

Ser Glu Leu Lys Pro His Asp Ala Ser Lys His Ile Tyr Tyr Thr Glu
                565                 570                 575

Val Ser Phe Ser Gly Val Leu Ile Tyr Pro Gly Gly Gln Ser Ala His
            580                 585                 590

Lys Lys Glu Val Gln Phe Arg Leu Ser Ala Pro Asp Gly Thr Ser Phe
        595                 600                 605

Trp Asn Pro Glu Asn Asp His Ser Tyr Gln Gly Leu Ser His Ala Leu
    610                 615                 620

Leu Lys Thr Arg Tyr Ile Pro Val Tyr Asp Asp Gly Arg Leu Val Phe
625             630                 635                 640

Gly His Glu Pro Gly Tyr
                645
```